United States Patent
McWhite

(10) Patent No.: US 11,583,490 B1
(45) Date of Patent: Feb. 21, 2023

(54) JEHOVAH-RAPHA MIRACLE HAIR OIL

(71) Applicants: Katie G. McWhite, Florence, SC (US); James W. Gasque, Columbia, SC (US)

(72) Inventor: Katie G. McWhite, Florence, SC (US)

(*) Notice: Subject to any disclaimer, the term of this patent is extended or adjusted under 35 U.S.C. 154(b) by 0 days.

(21) Appl. No.: 17/692,362

(22) Filed: Mar. 11, 2022

(51) Int. Cl.
*A61K 8/92* (2006.01)
*A61Q 5/00* (2006.01)

(52) U.S. Cl.
CPC .............. *A61K 8/922* (2013.01); *A61Q 5/00* (2013.01)

(58) Field of Classification Search
None
See application file for complete search history.

(56) References Cited

U.S. PATENT DOCUMENTS

2016/0346339 A1* 12/2016 Finley .................. A61K 31/355
2022/0249585 A1* 8/2022 Khubani .............. A61K 31/192

* cited by examiner

*Primary Examiner* — Nannette Holloman
(74) *Attorney, Agent, or Firm* — Melissa B. Neely

(57) ABSTRACT

The present invention is a hair oil developed with the hair care needs of African American women in mind. The invention is comprised of sweet almond oil, carrot oil, frankincense oil, cedarwood oil, orange oil, saffron oil, *gingko* oil, amla oil, neem oil, karanja oil, fo-ti oil, ginseng oil, green tea oil, onion seed oil, lemongrass oil, geranium oil, hyssop oil, clary sage, nettle leaf oil, myrrh oil, and chamomile oil.

2 Claims, No Drawings

JEHOVAH-RAPHA MIRACLE HAIR OIL

CROSS REFERENCE TO RELATED APPLICATIONS

None

STATEMENT REGARDING FEDERALLY SPONSORED RESEARCH OR DEVELOPMENT

This invention was not made by an agency of the United States Government nor under a contract with an agency of the United States Government.

THE NAME OF THE PARTIES TO JOINT RESEARCH AGREEMENT

Not Applicable.

INCORPORATION BY REFERENCE OF MATERIAL SUBMITTED ON A COMPACT DISC OR AS A TEXT FILE VIA THE OFFICE ELECTRONIC FILING SYSTEM (EFS-WEB)

Not Applicable.

STATEMENT REGARDING PRIOR DISCLOSURES BY THE INVENTOR OR A JOINT INVENTOR

Not Applicable

BACKGROUND OF THE INVENTION

Field of the Invention

Hair loss is common among African American women as well as issues with hair breakage, scalp itching, excessive dandruff and flaking. (African American Women, Hair Care and Health Barriers; Raechele Cochran Gathers and Meridith Grace Mahan; The Journal of Clinical and Aesthetic Dermatology, September 2014). Popular hair care products with African American women, including emollients (hair grease), gels, spritzers, and relaxers have been implicated in hair fragility and loss. (id)

These issues are prevalent among African American women. In a survey of African American women and white women, 60% of the African American women complained their hair was too dry compared to 67% of white women saying their hair had normal moisture. (https://www.webmd.com/beauty/news/20120321/african-american-women-have-specific-hair-issues, accessed Feb. 25, 2022).

The present invention is an all-natural hair oil formulated with the special needs of African American women in mind.

Description of Related Art

A number of US patents and published patent applications disclose formulations for hair care. Among them are U.S. patent Ser. No. 10/420,962, U.S. Pat. Nos. 9,066,952, 8,920,853, and 5,407,675. However, none of the prior art utilizes the number and variation of all natural essential oils as does the present invention.

BRIEF SUMMARY OF THE INVENTION

The present invention is a hair oil developed with the hair care needs of African American women in mind. The invention is comprised of sweet almond oil, carrot oil, frankincense oil, cedarwood oil, orange oil, saffron oil, *ginkgo* oil, amla oil, neem oil, karanja oil, fo-ti oil, ginseng oil, green tea oil, onion seed oil, lemongrass oil, geranium oil, hyssop oil, clary sage, nettle leaf oil, myrrh oil, and chamomile oil. Anecdotal evidence relates that this combination of essential oils is effective in the treatment of the hair issues plaguing African American women.

BRIEF DESCRIPTION OF THE SEVERAL VIEWS OF THE DRAWING

Not Applicable

DETAILED DESCRIPTION OF THE INVENTION

The present invention is a hair oil comprised of sweet almond oil, carrot oil, frankincense oil, cedarwood oil, orange oil, saffron oil, *gingko* oil, amla oil, neem oil, karanja oil, fo-ti oil, ginseng oil, green tea oil, onion seed oil, lemongrass oil, geranium oil, hyssop oil, clary sage, nettle leaf oil, myrrh oil, and chamomile oil.

Sweet almond oil is produced by pressing sweet almond nuts to acquire the oil. Sweet almonds contain vitamins A and E and are a source for fatty acids omega 6 and 9. Sweet almond oil can be used as a skin cleanser and moisturizer. It's moisturizing properties are good for scalp and hair health.

Carrot oil, also known as carrot seed oil, is most commonly used as a fragrance, flavoring, and food coloring. It has also had a range of applications in folk medicine and lab studies have shown that it acts as a muscle relaxant and vasodilator. (nutrawiki.org/carrot_oil/accessed on Feb. 25, 2022)

Frankincense is the resin or oil from the Boswellia tree and has been used by man for thousands of years. Although is possibly best known as one of the gifts of the Three Magi in the Bible, it was used by ancient Egyptians in the mummification process and other cultures as a medicine. Frankincense essential oil has been said to help in the prevention of hair loss and curing dandruff.

Cedarwood oil is extracted from the wood of a cedar tree. It has been recommended by herbalists as a treatment for thinning hair or hair loss. It is also used for treatment of a dry or flaky scalp as it can stimulate the scalp and increase circulation. (draxe.com/essential-oils/cedarwood-essential-oil accessed on Feb. 25, 2022)

Orange oil is extracted from the ring of the orange fruit. It is commercially available in many cleaning products and wood polishes or waxes. Like the fruit, orange oil is a source of vitamin C which can be absorbed by the scalp possibly resulting in improved circulation.

Saffron is a spice derived from the flower of the *Crocus sativus*. Saffron oil is produced by infusing the spice into a carrier oil. Saffron oil is known as a skin moisturizer and when applied to the hair is said to aid in the mending of damaged hair and the preventing of hair loss. (healthyfocus.org/amazing-benefits-of-saffron-oil, accessed Feb. 25, 2022)

*Ginkgo* oil is made from the leaves of a *Ginkgo biloba* tree, also known as the maidenhair tree. It has been used in traditional Chinese medicine and modern studies show that is both an antioxidant and vasodilator and may increase blood flow to the scalp. (www.hairguard.com/*ginkgo-biloba/*, accessed Feb. 25, 2022)

Amla oil is made from a fruit called Indian gooseberry. The oil is said to stimulate hair growth, prevent hair loss, reduce dandruff, and prevent premature graying of the hair. The Indian gooseberry is high in vitamin C. (Amla Oil: Benefits, Side Effects, and Preparations at verywellhealth.com), accessed Feb. 25, 2022)

Neem oil is a naturally occurring pesticide found in seeds from the neem tree also known as the Indian lilac or nimtree. (npic.orst.edu/factsheets/neemgen.html, accessed Feb. 25, 2022) Neem oil when applied to the hair is said to prevent dandruff, stop hair loss, improve hair texture, and stimulate hair growth. (www.organicfacts.net/neem-oil-for hair.html, accessed on Feb. 25, 2022).

Karanja oil is extracted from the pongam or karanja tree. Karanja oil is antibacterial and is known to promote wound healing. When applied to the hair, benefits of the oil include promotion of hair growth, protection of the skin and hair from UV damage, and smoothing of frizzy hair. (theskinverse.com/meet-karanja-oil-your-new-hair-and-skin-hero, accessed Feb. 25, 2022).

Fo-ti is used in Traditional Chinese Medicine. Fo-ti is also known as Chinese cornbind, fleeceflower, and Chinese knotweed. It has been used to prevent hair loss or thinning. (draxe.com/nutrition/fo-ti, accessed Feb. 25, 2022)

Ginseng is an ancient herbal remedy that has been in use for centuries. There is evidence that ginseng promotes hair growth and prevents hair loss. (Hair Growth Potential of Ginseng and Its Major Metabolites: A Review on Its Molecular Mechanisms, Bu Young Cho, International Journal of Molecular Sciences, September 2018)

Green tea oil is extracted from the seeds of the green tea plant. The oil is not the same as the popular beverage of green tea. Application of green tea oil to the hair is said to promote hair growth and inhibit hair loss. (anveya.com/blogs/top-tips/interesting-benefits-of-green-tea-oil-for-skin-hair-health, accessed Feb. 25, 2022)

Onion seed oil, also known as dark seed oil, is said to have benefits in the treatment of skin problems, various infections and other medical conditions. It is said to help reduce hair loss. (essentialoilbulk.com.enl/onion-seed-oil.html, accessed Feb. 25, 2022). Onion seed oil is not the same as onion oil.

Lemongrass oil is extracted from the leaves and stalks of the lemongrass plant. It is used in cooking, herbal medicine and a variety of skin care products like soaps, shower gels and shampoos. Lemongrass oil is said to strengthen hair follicles and relieve an irritated and itchy scalp. (draxe.com/essential-oils/lemongrass-essential-oil, accessed Feb. 25, 2022)

Geranium oil is extracted from the stems, leaves, and flowers of the geranium plant. The geranium is probably best known as a flowering annual in landscaping, flower pots, and hanging baskets. Geranium is used in herbal medicine for the treatment of skin infections both fungal and bacterial and an anti-inflammatory agent among other uses. The anti-inflammatory properties of geranium oil could aid in reducing inflammation of the scalp, which is a factor in chronic hair loss. (draxe.com/essential-oils/geranium-oils, accessed Feb. 25, 2022)

Hyssop oil is derived from the hyssop plant, which is often used in cooking. Hyssop oil has been used historically as a treatment for chest infections and other respiratory difficulties. It has a strong antiseptic action that could theoretically improve hair growth, but due to the strength of the oil it is not recommended as such. (www.vinevida.com/products/hyssop-essential-oil, accessed on Feb. 25, 2022)

The essential oil of clary sage is extracted from the buds and leaves of the clary sage plant. Clary sage oil increases hair growth and improve hair strength. (www.healthline.com/health/essential-oils-for-hair-growth, accessed Feb. 25, 2022)

Nettle leaf oil is extracted from the nettle leaf plant, also known as the stinging nettle, burn nettle and nettle. Nettle has been used for thousands of years as an herbal treatment for a variety of ailments. The anti-inflammatory property of nettle is beneficial in reducing inflammation of the scalp, which is a factor in chronic hair loss. (www.hairguard.com/stinging-nettle-for-hair-loss-results, accessed Feb. 25, 2022)

Myrrh oil is produced by steam distilling myrrh, the sap of the *Commiphora myrrha* tree. Myrrh has been used in Traditional Chinese medicine for centuries and is being studied for its potential uses in the treatment of pain, infections, and skin sores. (www.healthline.com/nutrition/myrrh-oil, accessed Feb. 25, 2022) Treatment of the hair with myrrh oil is said to moisturize a dry scalp and aid in preventing hair loss. (gyalabs.com/pages/guide-myrrh-oil-uses-benefits-skin-hair, accessed Feb. 25, 2022)

Chamomile oil is made from the flower of the chamomile plant. Chamomile oil is not the same as chamomile tea. Chamomile oil is known as a natural treatment for dandruff and can also be used to moisturize the hair and scalp.

The preferred embodiment of this invention is made by mixing the ingredients in the approximate quantities as shown in Table 1: Proportions of Ingredients in Preferred Embodiment of the Invention.

TABLE 1

Proportions of Ingredients in Preferred Embodiment of the Invention

| Ingredient | Ounces (fluid) | % Volume Range |
| --- | --- | --- |
| Sweet Almond Oil | 24 | 26-30 |
| Carrot Oil | 4 | 4-5.5 |
| Frankincense Oil | 2 | 2-2.6 |
| Cedarwood Oil | 4 | 4-5.5 |
| Orange Oil | 4 | 4-5.5 |
| Saffron Oil | 2 | 2-2.6 |
| Ginkgo Oil | 2 | 2-2.6 |
| Amla Oil | 4 | 4-5.5 |
| Neem Oil | 2 | 2-2.6 |
| Karanja Oil | 4 | 4-5.5 |
| Fo-ti Oil | 4 | 4-5.5 |
| Ginseng Oil | 4 | 4-5.5 |
| Green Tea Oil | 4 | 4-5.5 |
| Onion Seed Oil | 4 | 4-5.5 |
| Lemongrass Oil | 4 | 4-5.5 |
| Geranium Oil | 2 | 2-2.6 |
| Hyssop Oil | 2 | 2-2.6 |
| Clary Sage Oil | 2 | 2-2.6 |
| Nettle Leaf Oil | 2 | 2-2.6 |
| Myrrh Oil | 4 | 4-5.5 |
| Chamomile Oil | 2 | 2-2.6 |
| Total: | 86 | |

Although the composition of the preferred embodiment of the invention, it is anticipated that the composition of the invention could vary in the relative concentration of the ingredients. Table 2 provides the anticipated possible variation of the relative concentration of the ingredients for other embodiments of the invention.

TABLE 2

Compositional Ranges of Various Embodiments of the Invention

| Ingredient | % Volume Range |
|---|---|
| Sweet Almond Oil | 20-40 |
| Carrot Oil | 1-10 |
| Frankincense Oil | Trace-5 |
| Cedarwood Oil | 1-10 |
| Orange Oil | 1-10 |
| Saffron Oil | Trace-5 |
| Ginkgo Oil | Trace-5 |
| Amla Oil | 1-10 |
| Neem Oil | Trace-5 |
| Karanja Oil | 1-10 |
| Fo-ti Oil | 1-10 |
| Ginseng Oil | 1-10 |
| Green Tea Oil | 1-10 |
| Onion Seed Oil | 1-10 |
| Lemongrass Oil | 1-10 |
| Geranium Oil | Trace-5 |
| Hyssop Oil | Trace-5 |
| Clary Sage Oil | Trace-5 |
| Nettle Leaf Oil | Trace-5 |
| Myrrh Oil | 1-10 |
| Chamomile Oil | Trace-5 |

The present invention described above and in Table is visualized as one embodiment of the invention. It is envisioned that this invention may be embodied in many different forms and should not be construed as limited to the embodiments set forth herein. It will be understood by those skilled in the art that changes in details may be made without departing from the spirit and scope of the present application.

Suggested classifications for this invention include:
CUB 8/00: Essential oils, perfumes
A61K 8/00: Cosmetics or similar toilet preparations The terminology used herein is for describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated elements, and/or components, but do not preclude the presence or addition of one or more other elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The invention claimed is:

1. A hair oil consisting of 26 to 30% sweet almond oil, 4 to 5.5% carrot oil, 2 to 2.6% frankincense oil, 4 to 5.5% cedarwood oil, 4 to 5.5% orange oil, 2 to 2.6% saffron oil, 2 to 2.6% *ginkgo* oil, 4-5.5% amla oil, 2-2.6% neem oil, 4-5.5% karanja oil, 4-5.5% fo-ti oil, 4 to 5.5% ginseng oil, 4 to 5.5% green tea oil, 4 to 5.5% onion seed oil, 4 to 5.5% lemongrass oil, 2 to 2.6% geranium oil, 2 to 2.6% hyssop oil, 2 to 2.6% clary sage oil, 2 to 2.6% nettle leaf oil, 4 to 5.5% myrrh oil, and 2 to 2.6% chamomile oil.

2. A hair oil consisting essentially of 20 to 40% sweet almond oil, 1 to 10% carrot oil, trace to 5% frankincense oil, 1 to 10% cedarwood oil, 1 to 10% orange oil, trace to 5% saffron oil, trace to 5% *ginkgo* oil, 1 to 10% amla oil, trace to 5% neem oil, 1 to 10% karanja oil, 1 to 10% fo-ti oil, 1 to 10% ginseng oil, 1 to 10% green tea oil, 1 to 10% onion seed oil, 1 to 10% lemongrass oil, trace to 5% geranium oil, trace to 5% hyssop oil, trace to 5% clary sage oil, trace to 5% nettle leaf oil, 1 to 10% myrrh oil, and trace to 5% chamomile oil.

\* \* \* \* \*